United States Patent [19]

Anderson et al.

[11] Patent Number: 4,497,898

[45] Date of Patent: Feb. 5, 1985

[54] SPECTROPHOTOMETRIC METHOD FOR SIMULTANEOUSLY ANALYZING PROTEIN AND FAT CONTENTS IN MILK

[75] Inventors: Maynard E. Anderson, Hallsville; Robert T. Marshall, Columbia; Mark M. Hulse, Fulton, all of Mo.

[73] Assignee: The United States of America as represented by the Secretary of Agriculture, Washington, D.C.

[21] Appl. No.: 411,196

[22] Filed: Aug. 25, 1982

[51] Int. Cl.³ ..................... G01N 33/04; G01N 33/06
[52] U.S. Cl. ........................................ 436/23; 422/74
[58] Field of Search ............... 422/74, 81; 436/20–23, 436/86, 164; 356/435–436

[56] References Cited

U.S. PATENT DOCUMENTS

| | | | |
|---|---|---|---|
| 2,844,067 | 7/1958 | Borg | 88/14 |
| 2,950,396 | 8/1960 | Schneider | 250/219 |
| 3,098,717 | 7/1963 | Ferrari | 23/230 |
| 3,582,664 | 6/1971 | Hrdina | 356/435 X |
| 3,960,493 | 6/1976 | Beitz et al. | 23/230 B |
| 4,263,406 | 4/1981 | Bostick et al. | 435/291 |

OTHER PUBLICATIONS

Nakai et al., Spectrophotometric Determination of Protein and Fat in Milk Simultaneously; J. of Dairy Science, vol. 53, No. 3, 1970.

Huang et al., "Automated Modified Lowry Method for Protein Analysis of Milk," J. Food Sci. 41: 1219–1221 (1976).

Primary Examiner—Michael S. Marcus
Assistant Examiner—Michael S. Gzybowski
Attorney, Agent, or Firm—M. Howard Silverstein; David G. McConnell; Curtis P. Ribando

[57] ABSTRACT

By means of a novel triple-beam spectrophotometer, the protein and fat contents in milk can be simultaneously and rapidly determined. The system is self-compensating for discrepancies in the light path and for variations in lamp intensity, thereby yielding highly accurate analysis.

3 Claims, 3 Drawing Figures

SPECTROPHOTOMETRIC METHOD FOR SIMULTANEOUSLY ANALYZING PROTEIN AND FAT CONTENTS IN MILK

BACKGROUND OF THE INVENTION

1. Field of the Invention

The nutritional value of milk is associated predominantly with its protein and fat contents. While historically pricing has been based only upon the level of fat, increasing emphasis is now being placed on the percentage of protein as well. Accordingly, milk producers, dairy cattle breeders, and organizations such as the Dairy Herd Improvement Association (DHIA) require a quick and reliable method for determining the protein and fat contents of milk. The method should be applicable to assaying bulk lots as well as to samples collected daily from individual cows. For the on-site monitoring of individuals and small test groups, economics dictate a relatively simple procedure employing inexpensive and compact instrumentation. This invention relates to an automated assay method and apparatus designed specifically for this purpose.

2. Description of the Prior Art

An early batch-type photometric procedure for the determination of fat content in milk is taught by Borg in U.S. Pat. No. 2,844,067. A beam from a filtered light source is passed through emulsified samples and detected by a photoelectric cell. The percent fat is displayed on a meter as a function of the cell's output voltage. Calibration of the system is accomplished by regulation of the lamp intensity.

In U.S. Pat. No. 3,960,493, Beitz et al. provides a nephelometric method for the sequential determination of protein and fat in a milk sample. By addition of selective reagents, the protein and fat are alternately converted to colloidal dispersions, and each measured as a function of turbidity independent of the other.

Huang et al. [J. Food Sci. 41: 1219–1221 (1976)] report on a colorimetric procedure for assaying milk protein based on a modification of the Lowry method. Samples with and without the color-developing reagent are sequentially pumped into a flow-through cuvette, and in each case the absorbance is measured by means of a single-beam spectrophotometer. The difference in the respective absorbances null out the effect of the fat without any provision for determining its level.

While each of these prior art procedures are useful for its intended purpose, none combine the speed, accuracy, and versatility of multicomponent analysis presently demanded by many of the research and marketing activities of the dairy industry.

SUMMARY OF THE INVENTION

We have now discovered that by means of a novel triple-beam spectrophotometer, the protein and fat contents of milk can be simultaneously and rapidly determined with a high degree of precision. Two of the beams are trained on flow-through cuvettes to measure the respective transmittances of separate streams of a given milk sample: a sample stream with a reagent for developing a coloration intensity proportional to the level of protein, and a reference stream without the color-developing reagent. The third beam of the spectrophotometer monitors the intensity of the light source. By comparing the relative transmittance of the beams through the two streams to the relative transmittance of the beams through a baseline fluid such as water, the protein content can be accurately determined. Similarly, by comparing the relative transmittance of the reference beam and the monitoring beam during a period of milk sampling to the relative transmittance of the reference beam and the monitoring beam during a period of baseline determination, the fat content can be accurately measured. The protein and fat analyses are thereby independent of virtually all significant sources of error outside the samples themselves. For example, the system is self-compensating for day-to-day, long term, and intermeasurement changes in the light path attributable to disproportionate detector displacement from the light source, accumulation of residue in the cuvettes, and optical effects related to cuvette orientation. The system also compensates for intrameasurement variations in light source intensity caused by filament vibration, temperature changes, and line voltage fluctuation.

In accordance with this discovery, it is an object of the invention to provide a system for the continuous and rapid assay of milk samples for protein and fat.

It is also an object of the invention to provide a photometric method and apparatus for milk analysis which is self-compensating for all significant error factors and which is characterized by a high degree of precision.

Another object of the invention is to provide a milk assay system which is sufficiently simple and inexpensive to lend itself to widespread application in the dairy industry.

Other objects and advantages of this invention will become readily apparent from the ensuing description.

DETAILED DESCRIPTION OF THE INVENTION

The ensuing description of the invention will be based upon a modification of the standard Lowry method as the analytical procedure for developing a color intensity relative to the percentage protein present. The reagents employed in the modified method differ from those in the standard test only in that their strengths have been adapted to impart maximum sensitivity in a minimum reaction period. It is understood that other analytical procedures which correlate color intensity to protein content could be substituted herein for the modified Lowry method.

Figure 1:
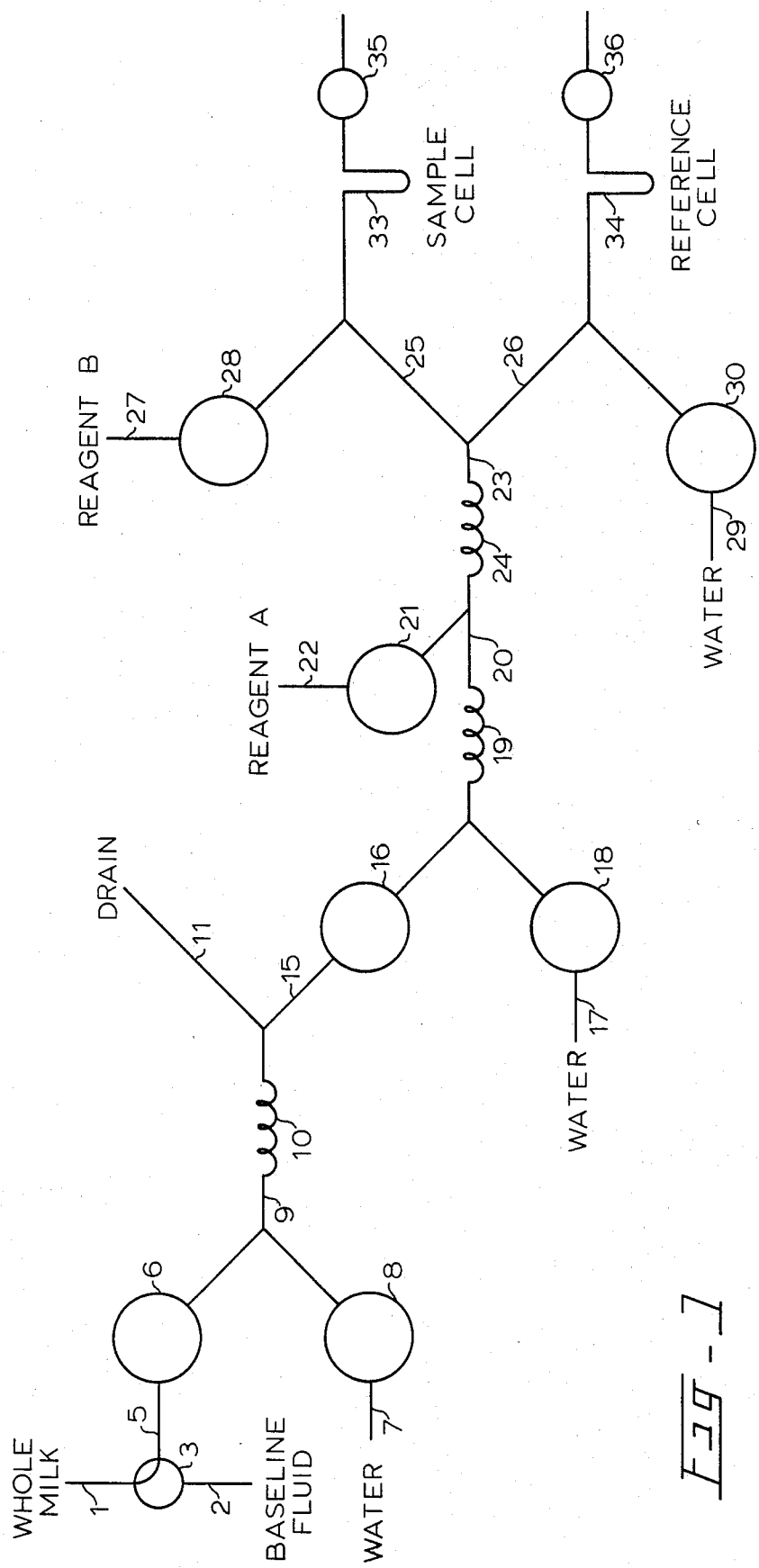
FIG. 1 is a flow diagram illustrating the pumping and mixing system for sample preparation.

Referring to FIG. 1, whole homogenized milk from a source not shown is supplied through line 1 and selectively admitted to the pumping and mixing system through three-way electrically-operated valve 3. Alternately, water or some other nonturbid, protein-free fluid supplied through line 2 is selectively admitted into the system for the purpose of establishing a baseline as described in further detail below. For the sake of clarity in the remaining description of the pumping system, the stream passing through line 5 will be referred to as the milk stream. The flow rate through line 5 is controlled by means of pump 6. Pump 8 in line 7 feeds diluent water into the system, also at a controlled rate, and the water and milk streams merge in line 9. While pump and line capacities are preselected to cause turbulent flow throughout the pumping system, it is desirable to include a mixing coil 10 in line 9 to insure homogeneity prior to diverting excess fluid to the drain via waste line 11. The remainder of the dilute milk stream is fed through line 15 by means of pump 16, and is again diluted with water pumped through line 17 by means of pump 18. Sample uniformity is promoted by means of mixing coil 19.

A buffered copper sulfate solution, hereafter referred to as Reagent A, is introduced through line 22 by means of pump 21. The solution is thoroughly mixed with the twice-diluted milk stream from line 20 under the aforementioned conditions of turbulent flow in line 23 with the aid of mixing coil 24. The flow is thereafter evenly split into a sample stream directed through line 25 and a reference stream directed through line 26. Reagent B, a phenol solution, is supplied through line 27 and is metered into the sample stream by means of pump 28. This reagent reacts with both the copper sulfate of Reagent A and the milk protein, and produces a bluish color with an intensity directly proportional to the percentage of protein in the sample. We have discovered that reproducible results are obtained well below the peak of color development, thereby permitting readings to be taken within 30 seconds of adding Reagent B. Water from line 29 and pump 30 is metered into the reference stream in an amount equivalent to that of Reagent B added to the sample stream. The respective streams entering flow-through cuvettes 33 and 34 thereby have the same solids content and turbidity level, and are identical in every respect except for the color-developing reagent in the sample stream. Flow meters 35 and 36 provide the proper degree of back pressure in lines 25 and 26 to control the even distribution therebetween of the stream from line 23, and to balance the flow through the cuvettes.

Table I below illustrates suitable reagent mixtures and Table II sets forth an exemplary mixing scheme. While we are not desiring to be limited to these values, we have found that they yield solutions compatible with the upper end of the sensitivity range of the photometric system described below. The high degree of milk dilution also serves to minimize consumption of the reagents. In the preferred operating mode of the invention, the milk reaching line 20 will have been diluted at least 100-fold.

TABLE I

| Reagent | Component | Parts by vol. (preferred) |
|---------|-----------|---------------------------|
| A | 10% (w/v) NaCO$_3$ | 20 |
|  | 5% (w/v) NaOH | 20 |
|  | 1% (w/v) CuSO$_4$.5H$_2$O | 1 |
|  | 3.75% (w/v) Na tartrate | 1 |
| B | Folin-Ciocalteau reagent | 1 |
|  | water | 5 |

TABLE II

| Pump | Pump rate (ml./min.) |
|------|----------------------|
| 6 | 5.16 |
| 8 | 18.06 |
| 16 | 5.16 |
| 18 | 143.62 |
| 21 | 5.16 |
| 28 | 5.16 |
| 30 | 5.16 |

Figure 2:
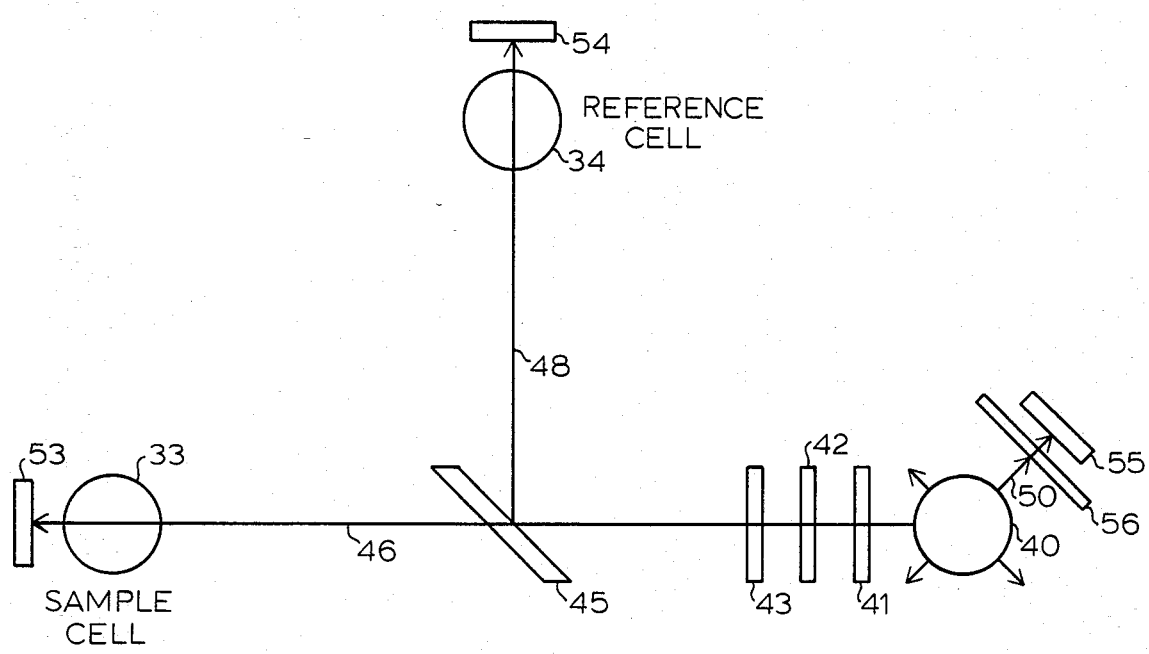
FIG. 2 is a schematic of the triple beam spectrophotometer for use in accordance with the invention.

The triple beam spectrophotometer is described in detail in FIG. 2. The three beams originate from a common light source 40. A tungsten or tungsten-halogen lamp would be suitable for use in conjunction with the Lowry analysis described above. A beam of light from the lamp is passed sequentially through an infrared filter 41 for removing the heat, a focusing lens 42, and a 740–760 nm. narrow band pass filter 43. The beam at the desired wavelength is thereafter divided into a pair of twin beams 46 and 48 by means of light beam splitter 45. Beam 46 is directed through the sample cell 33 to detector 53, and beam 48 passes through the reference cell 34 to detector 54. The light paths of the beams diverging from splitter 45 are preferably the same. That is, the respective cells and the respective detectors are equidistantly spaced from the point of divergence, and the optical properties of the cuvettes are matched to the extent practical.

A third beam 50 from common light source 40 is passed through a stable nonfluctuating path to detector 55. A semiopaque shield 56 is provided as protection against the high light intensity in close proximity to the lamp. The detectors contemplated for use herein are silicon photocells which characteristically have a linear current output.

Figure 3:
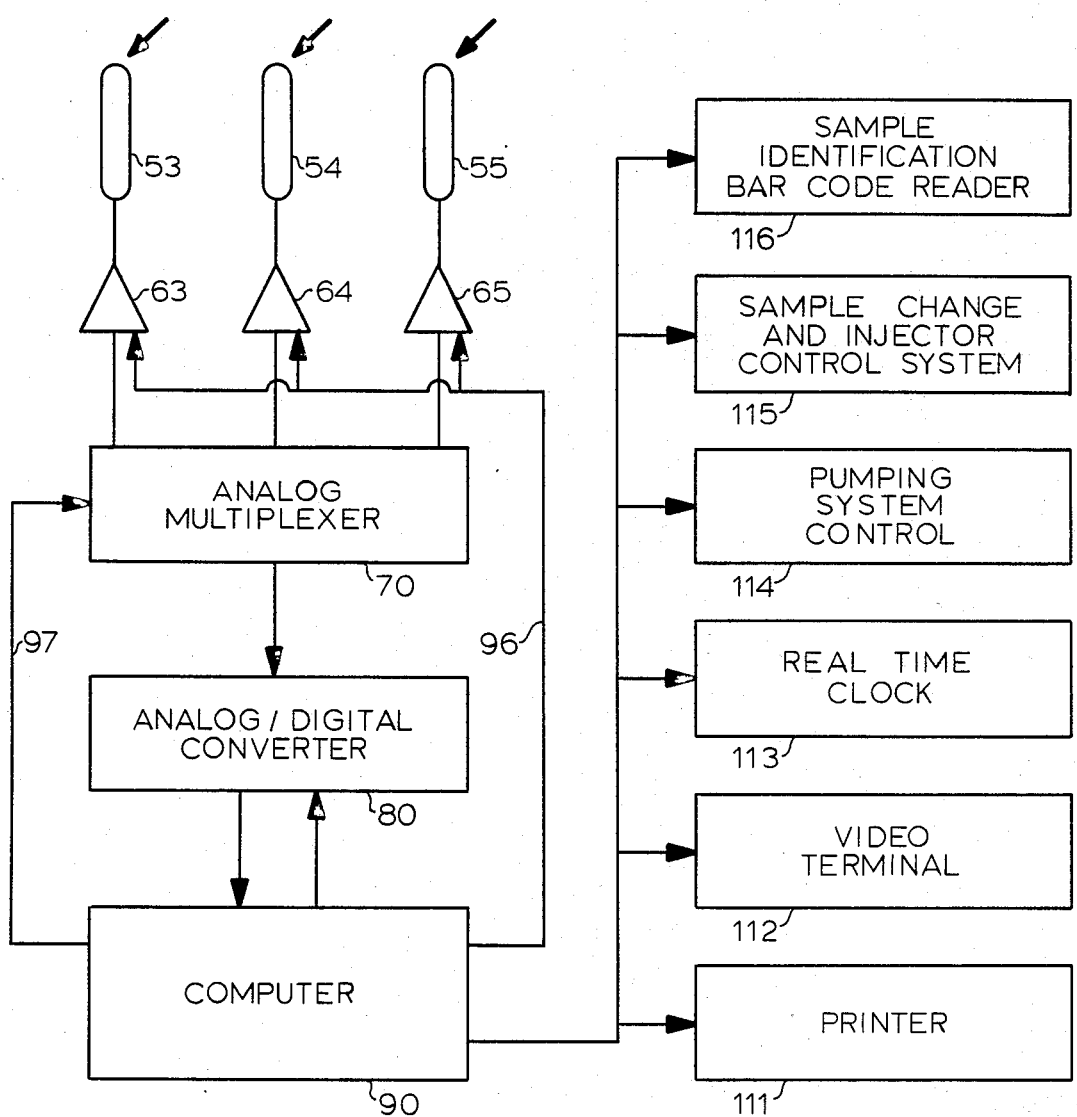
FIG. 3 is a block diagram of the data control system of the invention.

Referring to FIG. 3, the current output of each of the three silicon detectors is converted to voltage by converter amplifiers 63, 64, and 65. The amplifier gain is preselected to effect the greatest resolution by the hereinafter described analog/digital converter. By properly adjusting the gain of each amplifier with respect to the others, compensation for light path discrepancies is made. In a preferred embodiment of the invention, the use of programmable amplifiers would permit automatic gain adjustment. The analog voltage signals emitted by the amplifiers are transmitted via analog multiplexer 70 to the analog/digital converter 80. To be commensurate with the sensitivity of the remainder of the system, it is recommended that the converter 80 have at least 12-bit resolution. The digital output of the converter is thereafter fed into a microprocessor or other form of computer 90 for computational analysis of the protein and fat contents. Feedback circuit 96 is provided for use in conjunction with the aforementioned programmable amplifiers, and feedback circuit 97 is for computer control of the multiplexer 70. Accessories in communication with the computer include printer 111, video terminal 112, and a real-time clock 113. In a fully automated system, the computer can also be used to control the pumping system and the sample injection apparatus by means of controls 114 and 115, respectively. It is further envisioned that the computer be interfaced with bar code reader 116 for sample identification.

Prior to data collection, it is advisable to inject standardized solutions into the pumping and mixing system and to correct for light path discrepancies by gain adjustment of amplifiers 63, 64, and 65. Generation of a standardized curve at the predetermined assay temperature provides a basis for calculating the protein and fat contents from the raw transmittance data.

In operation, three-way valve 3 is controlled to admit either a milk sample from line 1 or a baseline fluid from line 2. Typically, a baseline will be taken before the first sample and then checked at periodic intervals throughout a sample series. Alternatively, the computer can be programmed to signal for a baseline check when an abnormal fluctuation in lamp intensity is detected. The milk samples and baseline fluid are similarly treated in the pumping systems by dilution and reagent addition as previously described. A transmittance reading is taken through each of the cells at a predetermined time after Reagent B is introduced into the sample stream. For enhanced reliability, an average may be computed from several readings taken over a time interval commensurate with a relatively stable portion of the color development curve. Concurrent with the recordation of transmittance data through the reference and sample cells, whether it be baseline data or sample data, the light intensity of the lamp 40 is monitored by means of detector 55.

It can be appreciated by reference to FIG. 1, that during periods of baseline check the only difference between the fluids in sample cell 33 and reference cell 34 would be the presence of distilled water in the reference cell in an amount equivalent to color-developing Reagent B in the sample cell. Similarly, during a period of milk sampling, the only difference between the fluids in the two cells is the presence in the sample cell of the color complex produced by the reaction of Reagent A, Reagent B, and the protein of the milk sample. The concentration of fat is identical in the respective streams.

It can further be appreciated that the transmittance through either of cells 33 or 34 during a period of milk sampling would differ from the transmittance through the same cell during a baseline check only as a result of constituents in the original milk sample not present in the baseline fluid. In the case of the reference stream, transmittance is affected predominantly by the light-scattering property of the fat. The extent of scattering and concomitant reduction in transmittance is correlated to the fat concentration. In the sample stream, the degree of light scattering attributable to fat content would be identical to that in the reference stream. Additionally, absorbance by the protein complex will have a significant effect on the transmittance through the sample cell.

Lambert's Law of Absorption dictates that the relationship between the original intensity $I_o$ of a light source and the intensity $I$ after passing through a material can be expressed as $$I = I_o e^{-kx}, \quad \text{(Equation 1)}$$

where x is the thickness of the material and k is the absorption coefficient. The transmittance of light is expressed as $$T = \frac{I}{I_o}. \quad \text{(Equation 2)}$$

For the purpose of best illustrating the advantage of the invention, $I_o$ is considered to represent the intensity at the beginning of the light path (at the light source 40), and I represents the intensity of the light striking the detector.

It becomes apparent that by comparing the relative transmittances of the sample beam 46 and reference beam 48 during a period of milk sampling ($T_{sm}/T_{rm}$) to the relative transmittances of the sample beam and reference beam during a period of baseline determination ($T_{sb}/T_{rb}$), all extraneous factors affecting the transmittance cancel out, leaving only the effect of the protein concentration. That is, the effect $E_p$ of the protein on transmittance is expressed by the ratio:

$$(T_{sm}/T_{rm}):(T_{sb}/T_{rb}); \text{ or} \quad \text{(Equation 3)}$$

$$E_p = \frac{T_{sm}}{T_{rm}} \times \frac{T_{rb}}{T_{sb}},$$

where the subscripts s and r refer to the sample and reference beams, respectively; and the subscripts m and b refer to periods of milk sampling and baseline determination, respectively.

By substituting Equation 2 for each transmittance term in Equation 3, we have:

$$E_p = \frac{(I_{sm}/I_{o-sm})}{(I_{rm}/I_{o-rm})} \times \frac{(I_{rb}/I_{o-rb})}{(I_{sb}/I_{o-sb})}. \quad \text{(Equation 4)}$$

By virtue of the original premise that $I_o$ is taken at the light source:

$$I_{o-sm} = I_{o-rm}; \text{ and}$$

$$I_{o-sb} = I_{o-rb}.$$

Equation 4 therefore reduces to:

$$E_p = \frac{I_{sm}}{I_{rm}} \times \frac{I_{rb}}{I_{sb}}. \quad \text{(Equation 5)}$$

Thus, for the relationship of transmittances expressed by Equation 3, only the final intensity reaching the detector need be considered. Referring to Equation 5, it is apparent that any factor, not directly related to a fluid stream and affecting one or the other of the light paths, would enter into both the numerator and the denominator, thereby cancelling itself out as previously mentioned. The same holds true for any factor commonly present in both the milk sample streams sm and rm, or in both the baseline medium streams sb and rb. By substituting the value of $E_p$, or its absorbance equivalent, into an equation established by passing standardized milk samples through the system, the protein content can be precisely ascertained.

The effect of fat on transmittance is similarly determined by utilizing the reference beam from the protein analysis as the sample beam for the fat analysis. The lamp monitoring beam 50 directed to detector 55 is now employed as a reference. Thus, by comparing the relative transmittance of the original reference beam 48 and the lamp beam 50 during a period of milk sampling ($T_{rm}/T_{lm}$) to the relative transmittances of the reference beam and the lamp beam during a period of baseline determination ($T_{rb}/T_{lb}$), the effect of the fat on transmittance can be isolated. That is, the effect $E_f$ of the fat on transmittance is expressed by the ratio:

$$(T_{rm}/T_{lm}):(T_{rb}/T_{lb}); \text{ or} \quad \text{(Equation 6)}$$

$$E_f = \frac{T_{rm}}{T_{lm}} \times \frac{T_{lb}}{T_{sb}},$$

where the subscripts r and l refer to the reference and lamp intensity monitoring beams, respectively; and the subscripts m and b again refer to periods of milk sampling and baseline determination, respectively.

By substituting Equation 2 for each transmittance term in Equation 6, we have:

$$E_f = \frac{(I_{rm}/I_{o-rm})}{(I_{lm}/I_{o-lm})} \times \frac{(I_{lb}/I_{o-lb})}{(I_{rb}/I_{o-rb})} \quad \text{(Equation 7)}$$

The original premise that $I_o$ is taken at the light source again dictates that:

$$I_{o-rm} = I_{o-lm}; \text{ and}$$

$$I_{o-rb} = I_{o-lb}.$$

Equation 7 therefore reduces to:

$$E_f = \frac{I_{rm}}{I_{lm}} \times \frac{I_{lb}}{I_{rb}} \quad \text{(Equation 8)}$$

As with $E_p$, $E_f$ is strictly a function of the detected beam intensities. The fat content can thereafter be computed by substituting the value of $E_f$, or its absorbance equivalent, into an equation established by passing standardized milk samples through the system.

The triple-beam spectrophotometer of this invention has the functional capability of two independent dual-beam spectrophotometers, in that it can be used for conducting referenced analysis of two components. That is, detector 54 provides a reference for detector 53 on the protein analysis, and detector 55 provides a reference for detector 54 in the fat analysis. The triple-beam concept as described herein is characterized by the added advantages of being immune from light path variances and fluctuations in lamp intensity. The resultant sensitivity enables protein and fat levels in the raw milk samples to be ascertained to 0.01% or better. Analyses can be completed in 20 seconds or less as compared to 40 minutes for the standard Lowry method for protein determination alone.

It is understood that the foregoing detailed description is given merely by way of illustration and that modification and variations may be made therein without departing from the spirit and scope of the invention.

We claim:

1. A method for the simultaneous determination of both the protein and fat contents of milk, said method comprising the steps of:
    a. providing a homogeneous dilute milk sample;
    b. dividing said sample into a sample stream and a reference stream;
    c. adding a color-developing reagent to said sample stream and reacting said reagent with the milk protein in said sample stream to impart a color thereto, wherein the intensity of said color is a function of the milk protein concentration;
    d. adjusting the solids concentration in said reference stream to correspond to that in the reagent-containing sample stream by dilution with an appropriate amount of water;
    e. simultaneously passing first and second light beams from a common source through said sample and reference streams, respectively, wherein said beams have a wavelength absorbable by the color imparted to said sample stream;
    f. continuously monitoring the intensity of said common light source by passing a third light beam from said source through a path of nonfluctuable transmissibility to a third detector;
    g. providing a nonturbid, protein-free fluid as a baseline fluid;
    h. dividing said baseline fluid into a first baseline stream having added thereto an amount of color-developing reagent equivalent to that added to the sample stream and a second baseline stream having added thereto an amount of water equivalent to that added to the reference stream;
    i. comparing the relative transmittance of said first and second beams at the time they are passed through said sample and reference streams to the relative transmittance of said first and second beams at the time they are simultaneously passed through said first and second baseline streams, and computing the protein content as a function of the ratio of said relative transmittances;
    j. comparing the relative transmittance of said second and third beams at the time said second beam is passing through said reference stream to the relative transmittance of said second and third beams at the time said second beam is passing through said second baseline stream, and computing the fat content as a function of the ratio of said relative transmittances.

2. The method as described in claim 1 wherein said color-developing reagent comprises a phenol which reacts with said milk protein and which also reacts with a buffered copper sulfate added to said dilute milk sample prior to said dividing step (b); and wherein the wavelength of said beams is in the range of 740–760 nm.

3. The method as described in claim 2 wherein said dilute milk sample comprises whole milk and water in a water:milk ratio of at least 100:1.

* * * * *